Figure 1:
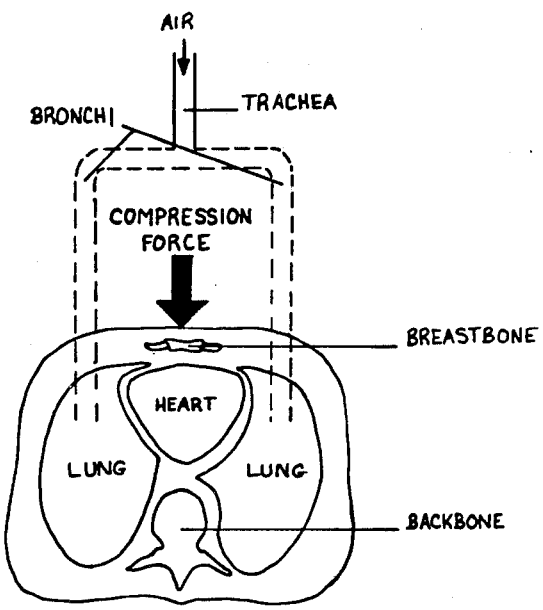

United States Patent [19]

Weisfeldt et al.

[11] 4,397,306
[45] Aug. 9, 1983

[54] INTEGRATED SYSTEM FOR CARDIOPULMONARY RESUSCITATION AND CIRCULATION SUPPORT

[75] Inventors: Myron L. Weisfeldt, Baltimore; Joshua E. Tsitlik, Reisterstown; Nisha Chandra, Towson, all of Md.

[73] Assignee: The John Hopkins University, Baltimore, Md.

[21] Appl. No.: 246,436

[22] Filed: Mar. 23, 1981

[51] Int. Cl.³ .................................... A61H 31/00
[52] U.S. Cl. .................................................. 128/28
[58] Field of Search ............... 128/24 R, 28, 30, 30.2, 128/205.25, 205.26; 434/265; 5/451

[56] References Cited

U.S. PATENT DOCUMENTS

| | | | |
|---|---|---|---|
| 3,078,842 | 2/1963 | Gray | 128/64 |
| 3,303,841 | 2/1967 | Dennis | 128/64 |
| 4,349,015 | 9/1982 | Alferness | 128/28 |

OTHER PUBLICATIONS

"Proceeding 8th Annual Northeast Bioengineering Conference"; *Instrumentation for Cardiopulmonary Resuscitation*; pp. 275-278.
"Cardiology"; *Time*; p. 29; Jan. 8, 1965.
Abstract of: *Carotid. Flow During Cardiopulmonary Resus.*; Am. Jur. Card., vol. 43, p. 422; Feb. 1979; by Applicants.
Full Text of: *Carotid. Flow*; Am. Jur. Card., vol. 48, p. 1053; Dec. 1981.

*Primary Examiner*—Richard J. Apley
*Assistant Examiner*—David Brown
*Attorney, Agent, or Firm*—Cushman, Darby & Cushman

[57] ABSTRACT

An integrated system for cardiopulmonary resuscitation and circulation support comprising chest compression means adapted to be positioned over the patient's sternum and operable to compress the sternum at desired intervals and to a desired degree, lung ventilating means including (1) a high pressure ventilator for ventilating simultaneously with chest compression; (2) a low pressure ventilator for inflating the lungs at low pressure between a selected number of compression cycles; and (3) a negative pressure ventilator for deflating the lungs between chest compressions; valve means for selectively operating only one of the indicated ventilators at any one time; means for restricting the abdomen to exert pressure on the abdominal wall; and control means for selectively operating the chest compression means, the lung ventilating means, valve means and abdomen restriction means in a selected sequence and for the period of time desired.

9 Claims, 7 Drawing Figures

MID-CHEST CROSS-SECTION

MID-CHEST CROSS-SECTION

MODEL OF BLOOD MOVEMENT ACCORDING TO CLASSICAL C.P.R. THEORY

TYPICAL PRESSURE DISTRIBUTATION DURING CHEST COMPRESSION (PRESSURES ARE IN mmHg)

TIMING DIAGRAM
FOR C.P.R. PROCEDURE

FUNCTIONAL DIAGRAM OF INTEGRATED CIRCUIT

INTEGRATED SYSTEM FOR CARDIOPULMONARY RESUSCITATION AND CIRCULATION SUPPORT

The present invention was made under contract or grant from the U.S. Department of Health and Human Services.

The invention is concerned with a novel and advantageous integrated system for cardiopulmonary resuscitation (CPR) and circulation support.

The use of CPR as a life-saving technique is well known. The ultimate goal of CPR is to maintain a supply of oxygenated blood to the brain and other vital organs, thus giving physicians time for restoration of heart activity by drug administration and other measures such as defibrillation or heart pacing.

To generate blood flow during CPR, blood has to be moved from within the thoracic structures to the periphery. In the conventional CPR technique, the breastbone (sternum) of the arrested patient is compressed at a typical frequency of 60 times per minute with a compression duration of 0.5–0.6 sec. The rescuer ventilates the patient's lungs during the chest release phase (CPR diastole) after every fifth compression either by forcing his own expired air into the patient's mouth or by an air bag-valve device.

While conventional CPR has been successfully employed, it has its deficiencies and there is considerable room for improvement. The principal object of the present invention is to provide such an improvement in terms of both apparatus and method. Other objects will also be apparent from the ensuing description.

The invention is hereinafter described in conjunction with the accompanying drawings where FIGS. 1–7 represent diagrammatic showings illustrative of the invention or background thereto.

The invention is based on a study of the mechanism of blood flow during CPR. The mechanism of blood movement originally suggested is illustrated in FIG. 1 which diagrammatically shows a cross section through the mid-chest. The heart lies between the breastbone and spine and is surrounded by the lungs. The classical theory of blood flow in CPR states that during chest compression the breastbone moves down squeezing the heart (like a rubber ball) and thus forcing the blood out of the heart into the aorta and further into peripheral blood vessels. The heart valves prevent retrograde flow. During chest release, the heart relaxes, and blood is drawn from the veins into the heart. This cycle of chest compression and release is repeated, typically 60 times/minutes, creating a semblance of flow.

Figure 2:
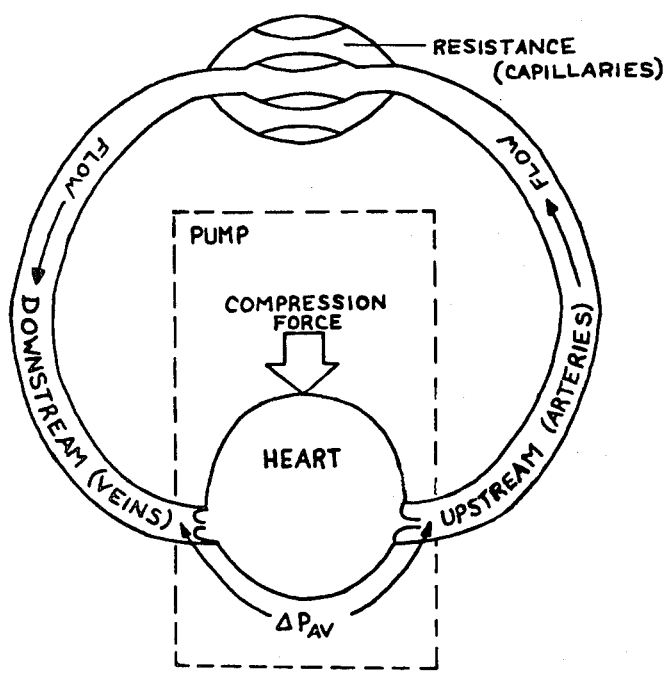

FIG. 2 shows a simple model of the described blood movement mechanism. The compressed heart appears as a pump. The upstream pipe represents the arteries, the downstream pipe the veins and the resistance is the capillaries. If the classical theory is correct, a pressure gradient (Pav) would exist across the pump (the compressed heart) between the upstream and downstream pipes. However, the studies leading to the present invention indicate that this is usually not the case.

Figure 3:
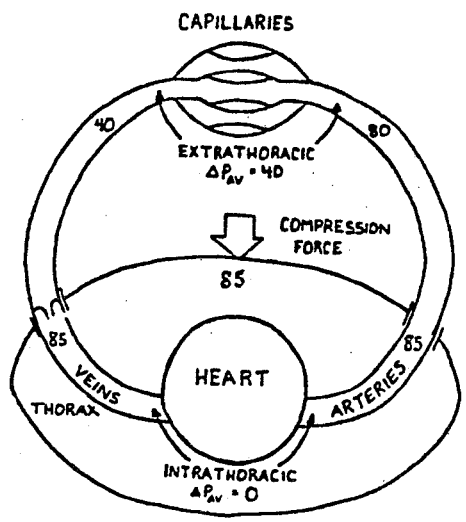

The typical pressure distribution during chest compression is represented in FIG. 3. Pressures in the thorax and in thoracic arteries and veins are equal. The pressure in the extrathoracic arteries is slightly lower than that in the thorax, but the pressure in the extrathoracic veins is markedly lower than that in the thorax. Therefore, the pressure gradient necessary for forward flow exists outside the chest and there is no pressure gradient between arteries and veins within the chest. The fact that there is no pressure gradient across the heart indicates that the heart cannot be serving as the pump.

It thus appears that, contrary to the previously accepted theory regarding blood flow in CPR, the mechanism of blood movement during external chest compression is not direct cardiac compression but is related to the increase in general intrathoracic pressure. Venous valves at the thoracic inlet prevent retrograde blood flow and lead to the lower extrathoracic venous pressure. Greater resistance to collapse of arteries than veins also results in better pressure transmission from the thorax to extrathoracic arteries. This phenomenon gives rise to a peripheral arteriovenous pressure gradient and antegrade flow.

As a consequence of these findings, the invention proposes a novel system for augmenting intrathoracic pressure in a cyclic fashion, and consequently augments blood flow. One feature of the present system includes means for ventilating the lungs at high airway pressure simultaneous with the chest compression which prevents over expansion of the lungs. This increases intrathoracic pressure during chest compression and thereby creates a larger peripheral pressure gradient and larger blood flow.

We have previously disclosed the concept of increasing intrathoracic pressure by ventilating at high airway pressure simultaneously with chest compression thus improving blood flow during CPR (The American Journal of Cardiology, Vol. 43, page 422, February 1979). It was found that the approach of utilizing ventilation at airway pressures of 70 to 110 cm $H_2O$ simultaneously with chest compression, markedly augmented blood flow, with no compromise in ventilation, even when compression was performed only 20 times per minute.

While the present system permits ventilation at high airway pressure simultaneous with chest compression, the system also incorporates certain other features which can substantially augment blood flow over and above that which is achieved with cyclical variations in intrathoracic pressure alone using chest compression and simultaneous ventilation. These other factors include tight binding of the abdomen with exertion of rather substantial amounts of abdominal pressure, negative diastolic airway pressure ventilation to move greater amounts of blood into the chest during diastole and administration of large amounts of intravenous fluids. Additionally, it is important to provide means for ventilation at low positive airway pressure independent of compression and/or high airway pressure ventilation.

Broadly described, the system of the invention comprises chest compression means adapted to be positioned over the patient's sternum and operable to compress the sternum at desired intervals and to a desired degree, lung ventilating means including (1) a high pressure ventilator for ventilating simultaneously with chest compression; (2) a low pressure ventilator for inflating the lungs at low pressure after a selected number of compressions; and (3) a negative pressure ventilator for deflating the lungs between compressions and/or generating negative pressure in the thorax; valve means for selectively operating any one of the indicated ventilators at any one time; means for restricting the abdomen to exert pressure on the abdominal wall; and control means for selectively operating the chest compression means, the lung ventilating means, valve means and abdomen restriction means in the sequence and for the time desired.

The system also advantageously includes data acquisition and display means operatively associated with the control means for determining or varying the operation of the compression and ventilating means as required.

Equipment for monitoring ECG and other vital signs may also be included.

The system has versatile functions. For example, it can perform: (1) chest compression/restriction synchronized with the patient's ECG at frequencies determined by the control means; (2) airway occlusion synchronous with compression, or high pressure ventilation simultaneous with restriction; and (3) separate intermittent diastolic ventilation or negative airway pressure interposed between high airway pressure cycles. The system also has associated safety features which prevent the administration of high airway pressures without the performance of simultaneous chest restriction.

An important advantage of the present system is that in addition to being useful for CPR in the case of cardiac arrest, it can also be used in patients with circulatory difficulties such as cardiogenic shock. Cyclical high intrathoracic pressure timed to the cardiac cycle can be used to augment peripheral perfusion and decrease the work load of the heart.

It is to be noted that the present system can essentially be made up of commercially available elements, possibly with some relatively straightforward modifications or adjustments. For example, in one embodiment of the invention, a chest compression device is used. Such a device ("Thumper") is well known and available from Michigan Instruments, Grand Rapids, Mich. This device, which is extensively used for cardiopulmonary resuscitation, provides a means for external compression of the adult human chest with sufficient force to move the sternum approximately two inches in an anterior posterior direction. This is performed at a rate of 60 times/minute with 50% compression duration. The device is able to provide independent ventilation at low or appropriate airway pressures at a rate of approximately 16 times/minute interposed between compressions. While the present invention may use the "Thumper" in one aspect of the invention, the overall system described herein is intended to provide an improved means for the resuscitation of patients with a decreased incidence of complications and which can also be used for circulatory support.

Figure 4:
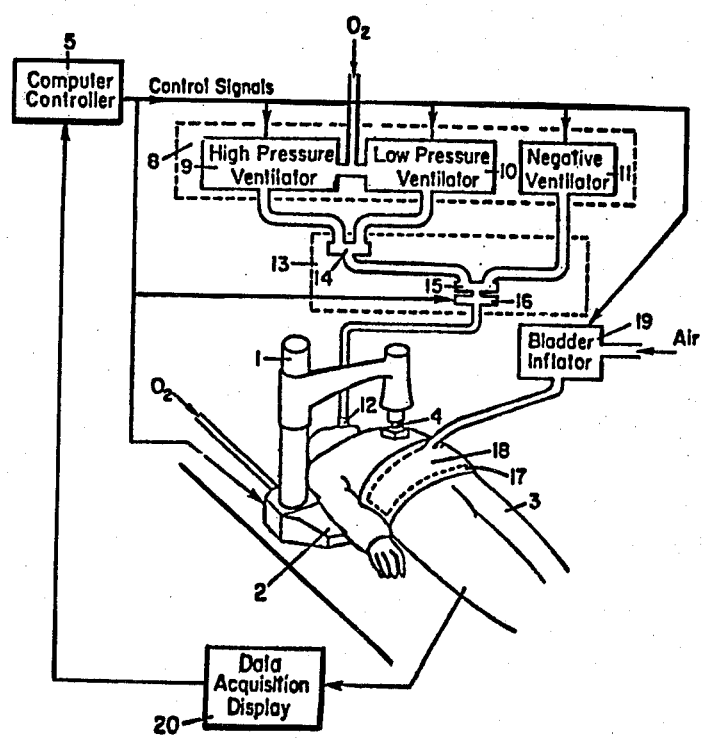
Figure 5:
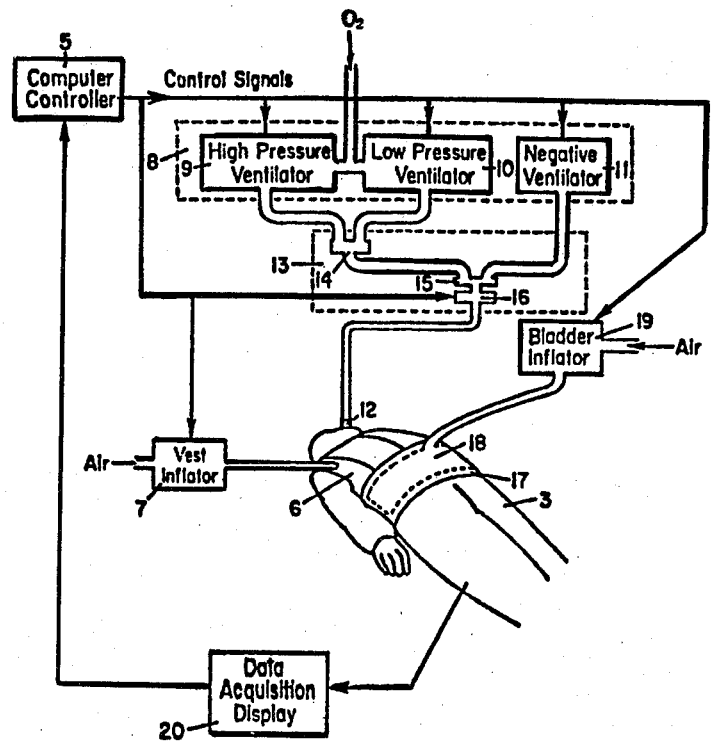

The system of the invention is more fully described in block form in FIGS. 4 and 5. As shown, and with particular reference to FIG. 4, the system includes as the chest compression or restriction means, a commercially available "Thumper" device (1) as mentioned earlier. This device is equipped with a metal back piece (2) which fits behind the thorax of the patient (3). The patient is placed under the device in the supine position and the chest compressor (1) is positioned over the sternum. It is then pneumatically energized and by manual adjustment of the compression force the piston (4) is set to compress the sternum to the desired degree, e.g., approximately two inches. The device is operatively associated with a controller (5) so that switching on and off of the chest compressor is conducted by electrical signals from the controller. The device (1) repeats the desired chest compression at a programmed controlled rate (10, 20, 40 or 60 times/minute) and with a controlled compression duration (usually 60% of the cycle).

FIG. 5 shows generally the same system as FIG. 4 except that, in lieu of the device (1) of FIG. 4, a different type of chest compression device, namely an inflatable vest (6), is used. The vest may be inflated by a vest inflator (7) controlled by means (5).

The system of FIGS. 4 and 5 also includes lung ventilation means, generally designated by the numeral (8) and set off by the broken lines. These means comprise a high pressure ventilator (HPV) (9), a low pressure ventilator (LPV) (10) and a negative pressure ventilator (NPV) (11). The system ventilates the patient's lungs through an endotracheal tube (12) placed in the patient's trachea. The HPV (9) delivers ventilation simultaneous with chest compression to increase intrathoracic pressure. It provides manually adjusted airway pressures of 70 to 110 cm of water. The LPV (10) inflates the lungs at appropriate low pressures (e.g. 20 to 50 cm of water) between compressions after every preprogrammed number (from 3 to 10) of compression cycles. The NPV (11) deflates the lungs between compression cycles and produces negative pressure in the thorax.

As shown, means are included for feeding oxygen (oxygen-containing gas) into the ventilation system. Usually carbon dioxide will also be mixed with the oxygen as will be understood by those in the art.

The system also includes valve means (14), (15) and (16). Of these, valve (14) couples together both positive ventilators HPV (9) and LPV (10), while valve (15) is an inspiration-expiration valve which connects the positive ventilators and the NPV (11) to endotracheal tube (12). Valve (15) allows a variable amount of negative airway pressure to be added to the other components of the system without changing any of the other components of the system including the level of positive high airway pressure ventilation. The controlled valve (16) allows occlusion of the airway synchronous with compression.

The system additionally includes abdomen restriction means including abdominal garment (17), inflatable bladder (18) within the garment, and device (19) for inflating the bladder. The garment (17) is designed to cover the area from the lower chest wall to below the pelvic brim. The bladder (18) allows variable amounts of pressure to be exerted on the external aspects of the abdominal wall and the bladder inflator (19) allows inflation of the bladder to the desired pressure value. Advantageously, the bladder inflator (19) is controlled by the control means (5).

The control means (5) is used to control any or all of the chest compression, ventilating, valve and abdomen restricting means, as well as any other devices which might be added to the basic system as outlined above. Factors which can be controlled by the controller are (1) compression rate and duration, (2) high airway pressure ventilation rate and duration, (3) low airway pressure ventilation rate and duration interposed between compression and high airway pressure ventilation compression cycles, (4) negative airway pressure ventilation rate and duration during diastole, (5) airway occlusion rate and duration, (6) degree of abdomen restriction, including possibly an abdomen counter pulsating system to be inflated out of cycle with the high airway pressure and ventilation system.

Advantageously the controller means (5) may comprise a microcomputer based, for example, on a Motorola 6800 microprocessor. To fulfill requirements for immediate change of multiple variables and to prevent possible errors when controlling the system during a patient's cardiac arrest, it may be advantageous to provide the controller means with a limited number of control switches each of which is concerned with a particular preprogrammed CPR procedure.

The system of FIGS. 4 and 5 additionally includes data acquisition and display means (20) which may comprise one or more recorders, pressure and flow transducers, flow rate and velocity meters and an ECG discriminator. This part of the system allows the physician to assess and choose the most efficient procedure of ventilation or support and may also be used to supply the controller (5) with the signals needed to synchronize the compressions with the patient's ECG.

Figure 6:
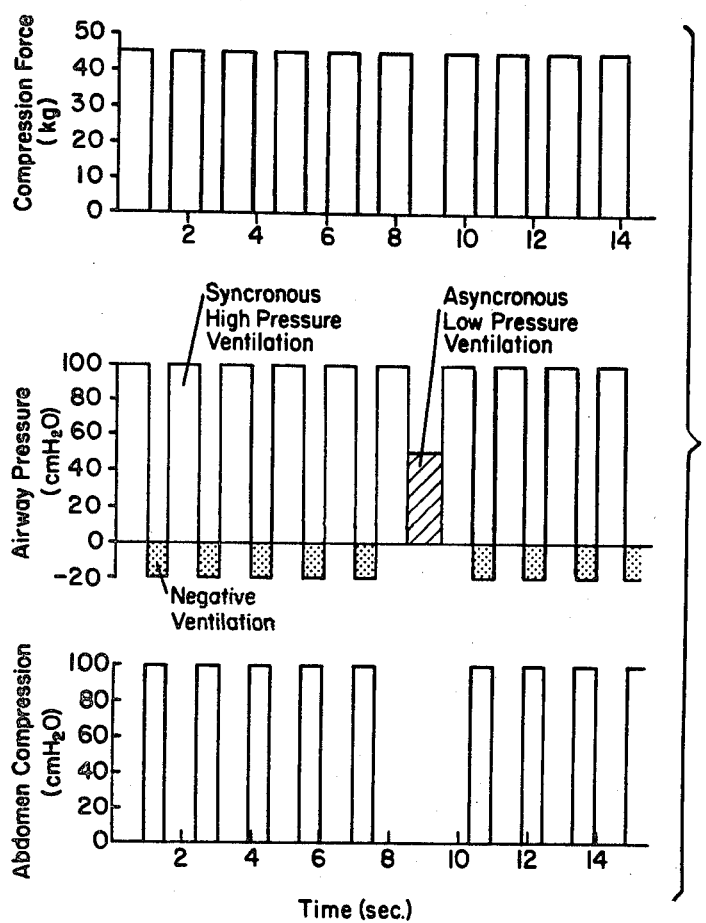

It will be recognized that the present system lends itself to a variety of operations which may be chosen to fit the particular needs of a patient undergoing CPR or circulatory support. One representative method according to the invention may include (1) a series of chest compressions coupled with simultaneous or synchronous high pressure airway ventilation; (2) negative ventilation at the intervals when chest compression is not applied; (3) periodic application of asynchronous low pressure ventilation in lieu of negative ventilation following the application of steps (1) and (2); and (4) abdomen restriction coupled with negative ventilation. This sequence of operations is illustrated in FIG. 6 which shows a representative sequence and timing for chest compression, ventilation and abdomen compression. Representative degrees of compression and pressures are also shown. Time is given in seconds, chest compression in kg, ventilation (or airway pressure) in centimeters of water and abdomen compression in centimeters of water.

Figure 7:
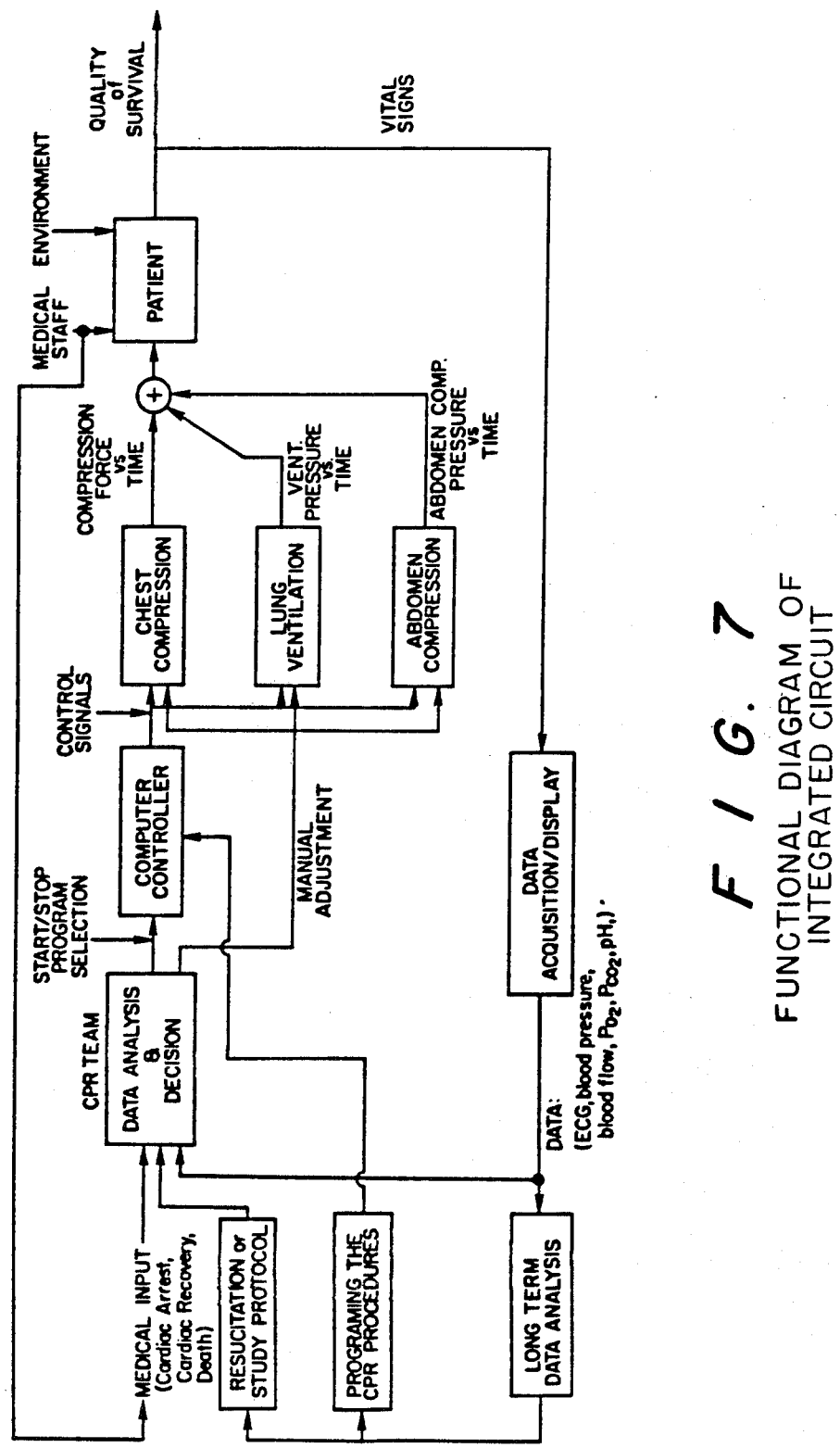

The manner in which the above-described system works is illustrated in FIG. 7. The CPR team receives the necessary information from the medical housestaff and as a feedback from the data acquisition and display subsystem and sets up the best procedure for resuscitation. The members of the team manually adjust the magnitude of the various parameters. The computer controller outputs the appropriate time signals to the chest compressor, different ventilators and abdominal system which are employed during the resuscitation.

Simultaneous with the CPR team, the medical housestaff conducts its part of the patient's resuscitation effort. The aim of the resuscitation effort is to improve the quality of the patient's survival and his functional return to life.

The system has two feedback loops. One serves as an information source about the efficacy of CPR during the run. It allows choice of the proper procedure from available hemodynamic data. Second, the long term data analysis makes possible the evaluation of conducted CPR and development of new CPR protocols and procedures with subsequent loading of new procedures into the controller.

Use of the system indicates an additive beneficial effect of (1) ventilation at high airway pressures simultaneous with chest compression; (2) abdominal binding; (3) negative airway pressure between compression ventilation cycles; and (4) volume loading with intravenous fluids. In laboratory tests it has been shown that a 4-fold increase in carotid arterial blood flow can be obtained over that produced by conventional CPR when using the system of the invention.

The system of the invention provides precise control of such variables as chest compression, synchronous ventilation, asynchronous, diastolic negative ventilation and abdomen compression. It is also possible to vary frequency, direction, phase relationship and magnitude with respect to each of these variables. The system permits a precise sequencing of operations with assured reproducibility whether used for CPR or for circulatory support.

It will be appreciated that various additional features other than those shown in the drawings may be included in the system of the invention. Reference has been made above to ECG and the system will usually include ECG means (not shown) for connection with the patient and the controller means (5) in order to analyze the ECG and make whatever adjustments seem appropriate in the degree and sequence of chest compression, ventilation and/or abdomen restriction. Other modifications of the basic system outlined above may also be incorporated. Hence the scope of the invention is defined by the following claims wherein:

What is claimed is:

1. An integrated system for cardiopulmonary resuscitation and circulation support comprising chest compression means adapted to be positioned over the patient's sternum and operable to compress the sternum at desired intervals and to a desired degree, lung ventilating means including (1) a high pressure ventilator for ventilating simultaneously with chest compression; (2) a low pressure ventilator for inflating the lungs at low pressure between a selected number of compression cycles; and (3) a negative pressure ventilator for deflating the lungs between chest compressions; valve means for selectively operating only one of the indicated ventilators at any one time; means for restricting the abdomen to exert pressure on the abdominal wall; and automatically operable control means for selectively operating the chest compression means, the lung ventilating means, valve means and abdomen restriction means in a predetermined selected sequence and for the period of time desired.

2. The system of claim 1 including data acquisition and display means operatively associated with the control means for determining and varying the operation of said compression and ventilating means as required.

3. A system according to claim 1 including means for monitoring ECG associated with said controller.

4. A system according to claim 1 wherein the chest compression means includes a thumper.

5. A system according to claim 1 wherein the chest compression means includes an inflatable jacket.

6. A system according to claim 1 wherein the abdomen restriction means applies constant restriction.

7. A system according to claim 1 wherein the control means comprises a computer.

8. A system according to claim 1 wherein the abdomen restriction means applies pulsating restriction.

9. A method for carrying out cardiopulmonary resuscitation and circulation support in accordance with and utilizing the apparatus of claim 1 comprising the steps of applying a series of chest compressions simultaneously with high pressure airway ventilation; applying negative ventilation at the intervals when chest compression is not applied; periodically applying a synchronous low pressure ventilation in lieu of negative ventilation and restricting the abdomen simultaneously with the application of negative ventilation.

* * * * *